(12) United States Patent
Brown

(10) Patent No.: US 9,095,981 B2
(45) Date of Patent: Aug. 4, 2015

(54) LOAD AND TORQUE RESISTANT CALIPER EXOSKELETON

(71) Applicant: Garrett W. Brown, Philadelphia, PA (US)

(72) Inventor: Garrett W. Brown, Philadelphia, PA (US)

(*) Notice: Subject to any disclaimer, the term of this patent is extended or adjusted under 35 U.S.C. 154(b) by 0 days.

(21) Appl. No.: 14/371,334

(22) PCT Filed: Jan. 10, 2013

(86) PCT No.: PCT/US2013/020974
§ 371 (c)(1),
(2) Date: Sep. 26, 2014

(87) PCT Pub. No.: WO2013/106532
PCT Pub. Date: Jul. 18, 2013

(65) Prior Publication Data
US 2015/0016923 A1 Jan. 15, 2015

Related U.S. Application Data

(60) Provisional application No. 61/585,424, filed on Jan. 11, 2012.

(51) Int. Cl.
*F16M 13/04* (2006.01)
*G03B 17/56* (2006.01)
*B25J 13/00* (2006.01)
*A61F 5/01* (2006.01)
*B25J 9/00* (2006.01)
*B66F 11/00* (2006.01)

(52) U.S. Cl.
CPC . *B25J 13/00* (2013.01); *A61F 5/01* (2013.01); *B25J 9/0006* (2013.01); *B66F 11/00* (2013.01); *F16M 13/04* (2013.01); *G03B 17/561* (2013.01)

(58) Field of Classification Search
CPC .............................. B25J 9/0006; F16M 13/04
USPC .................................................. 396/420, 421
See application file for complete search history.

(56) References Cited

U.S. PATENT DOCUMENTS 3,449,769 A 6/1969 Mizen
3,923,166 A 12/1975 Fletcher et al.
3,964,182 A 6/1976 Pomeret et al.
(Continued)

FOREIGN PATENT DOCUMENTS

CN 202682285 1/2013
GB 1188647 4/1970
(Continued)

OTHER PUBLICATIONS

International Search Report and Written Opinion dated May 6, 2013 for PCT/US2013/020974.
(Continued)

*Primary Examiner* — Justin Larson
(74) *Attorney, Agent, or Firm* — Barnes & Thornburg LLP; Joan T. Kluger

(57) ABSTRACT

An exoskeleton assembly having an upper body support assembly pivotally connected to a lower body support assembly. A caliper assembly is connected to the lower and upper body support assemblies and includes a load arm attached to a differential strut. The caliper assembly has links pivotally attached to the upper and lower body assemblies. Pistons attached to the load arm substantially maintain a mounting component in an upright position.

8 Claims, 12 Drawing Sheets

(56) References Cited

U.S. PATENT DOCUMENTS

| | | | |
|---|---|---|---|
| 4,208,028 A * | 6/1980 | Brown et al. | 224/185 |
| 4,394,075 A * | 7/1983 | Brown et al. | 352/243 |
| RE32,213 E * | 7/1986 | Brown | 352/243 |
| 4,957,320 A | 9/1990 | Ulrich | |
| 5,360,196 A | 11/1994 | DiGiulio et al. | |
| 5,435,515 A * | 7/1995 | DiGiulio et al. | 248/576 |
| 6,355,335 B1 | 3/2002 | Kulkaski | |
| 6,666,796 B1 | 12/2003 | MacCready, Jr. | |
| 6,764,231 B1 | 7/2004 | Shubert | |
| 6,923,505 B2 | 8/2005 | Siminovitch et al. | |
| 7,445,138 B2 * | 11/2008 | Chu | 224/637 |
| 7,571,839 B2 * | 8/2009 | Chu et al. | 224/637 |
| 7,857,774 B2 * | 12/2010 | Sankai | 601/5 |
| 8,060,945 B2 * | 11/2011 | Adarraga | 2/22 |
| 8,142,083 B2 * | 3/2012 | Brown | 396/421 |
| 8,171,570 B2 * | 5/2012 | Adarraga | 2/22 |
| 8,474,672 B1 * | 7/2013 | Keith | 224/576 |
| 8,506,180 B2 * | 8/2013 | Brown | 396/421 |
| 8,641,782 B2 * | 2/2014 | Kim et al. | 623/58 |
| 8,932,241 B2 * | 1/2015 | Sankai | 601/35 |
| 8,968,222 B2 * | 3/2015 | Kazerooni et al. | 601/35 |
| 8,985,878 B2 * | 3/2015 | Di Leo | 396/422 |
| 2003/0004444 A1 | 1/2003 | Perner et al. | |
| 2003/0223844 A1 * | 12/2003 | Schiele et al. | 414/5 |
| 2005/0258210 A1 * | 11/2005 | Chu | 224/637 |
| 2005/0279796 A1 * | 12/2005 | Chu et al. | 224/637 |
| 2006/0260620 A1 | 11/2006 | Kazerooni et al. | |
| 2007/0056592 A1 | 3/2007 | Angold et al. | |
| 2007/0241696 A1 | 10/2007 | Lauria et al. | |
| 2009/0210093 A1 | 8/2009 | Jacobsen et al. | |
| 2010/0059652 A1 * | 3/2010 | Brown | 248/585 |
| 2010/0254696 A1 | 10/2010 | McKay | |
| 2011/0066088 A1 * | 3/2011 | Little et al. | 601/35 |
| 2011/0164949 A1 * | 7/2011 | Kim et al. | 414/1 |
| 2011/0166489 A1 | 7/2011 | Angold et al. | |
| 2011/0214524 A1 | 9/2011 | Jacobsen | |
| 2011/0266323 A1 | 11/2011 | Kazerooni et al. | |
| 2012/0292361 A1 * | 11/2012 | Thiruppathi | 224/576 |
| 2013/0102935 A1 * | 4/2013 | Kazerooni et al. | 601/35 |
| 2013/0158445 A1 * | 6/2013 | Kazerooni et al. | 601/35 |
| 2013/0228602 A1 * | 9/2013 | Thiruppathi | 224/625 |
| 2013/0303950 A1 * | 11/2013 | Angold et al. | 601/35 |
| 2014/0064720 A1 * | 3/2014 | Chapman | 396/428 |
| 2014/0100493 A1 * | 4/2014 | Craig et al. | 601/35 |
| 2014/0121573 A1 * | 5/2014 | Kazerooni et al. | 601/23 |
| 2014/0200491 A1 * | 7/2014 | Julin et al. | 601/35 |
| 2014/0276261 A1 * | 9/2014 | Caires et al. | 601/33 |
| 2014/0276264 A1 * | 9/2014 | Caires et al. | 601/34 |
| 2014/0276265 A1 * | 9/2014 | Caires et al. | 601/34 |
| 2014/0366323 A1 * | 12/2014 | Brown et al. | 16/322 |
| 2015/0001269 A1 * | 1/2015 | Sacksteder | 224/576 |
| 2015/0016923 A1 * | 1/2015 | Brown | 414/1 |
| 2015/0048134 A1 * | 2/2015 | Fawcett et al. | 224/576 |
| 2015/0076196 A1 * | 3/2015 | Brown et al. | 224/271 |

FOREIGN PATENT DOCUMENTS

| | | |
|---|---|---|
| WO | 2010101595 | 9/2010 |
| WO | 2011127471 | 10/2011 |

OTHER PUBLICATIONS

Kreft, E. "This is the First Robotic Exoskeleton Ever Approved for Home Use" [online], Jul. 2014. Retrieved from the Internet: <URL: http://www.theblaze.com/stories/2014/07/01/this-is-the-first-robotic-exoskeleton-ever-approved-for-home-use/FDA article>.
International Search Report and Written Opinion dated Aug. 6, 2012 for PCT/US2012/036581.

* cited by examiner

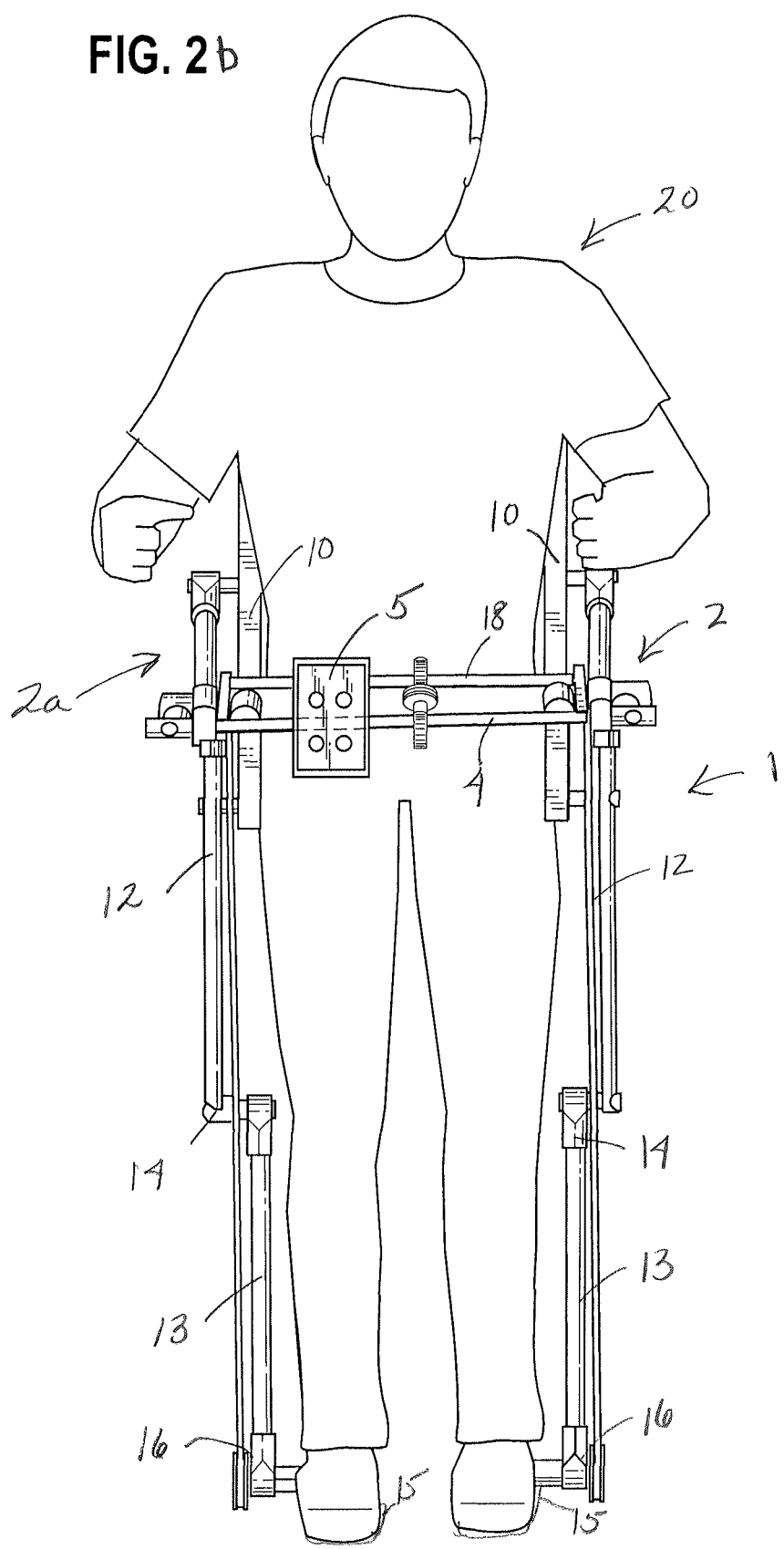

LOAD AND TORQUE RESISTANT CALIPER EXOSKELETON

BACKGROUND OF THE INVENTION

Human load-bearing has been facilitated throughout history by appliances attached to the human frame. These have included head-mounted tump-lines and body-mounted front, side, and back-packs, for burdens as light as a 'papoose' and as heavy as a hundred kilos of stone or wood.

Excepting the tump-line, all such load-bearing appliances must resist loads that, depending on their size and shape, are at least minimally displaced (cantilevered) away from the human frame and thus may cause the additional strain of a torque load on the upper body.

A problematic sub-category of cantilevered loads, including historical weaponry, flags and banners etc., involves objects positioned farther out in front of the torso, which therefore, place additional torque upon the structure and musculature of the human back—such as particularly the erector spinae muscles which flank the spine. This sub-category of burdens recently includes available assemblies which cantilever stabilized cameras and heavy industrial tools variably far out in front of their human operators. Operators of devices 'floating' on such equipoising arms are unable to squat or even bend forward without having to physically restrain their payloads from lurching away due to the action of gravity upon no-longer-vertical hinge pins, and enduring the added strain of eventually standing back upright while so burdened.

Fortunately, recent advances in bio-mechanics have yielded relatively lightweight exoskeletal appliances that can be 'worn' by humans and tirelessly facilitate ambulatory weight-carrying. These devices, teamed with adjunct Steadicam-type arms, can also indefinitely resist cantilevered torque loads, but they are all complicated, expensive and power-hungry—to such extent that a sizable portion of their payload capability must include batteries, fuel-cells or even generators if they are to be operated in a self-contained manner without being tethered to an external power source.

What is needed is a passive, human-wearable appliance that supports cantilevered loads for extended periods of time with relatively little or no strain on the upper body.

What is needed is a human-wearable exoskeletal appliance that resists cantilevered loads by countering them with the leaning-back mass of the entire body, transmitting the weight burden to the ground.

Also needed is a human-wearable exoskeletal appliance that supports cantilevered loads, yet operates passively, without powered actuation requiring onboard or external sources of energy.

And also needed is an exoskeletal appliance that permits leaning or squatting while substantially preserving the relative verticality of associated equipoising arm hinge-pins, and optionally provides powered assistance for returning to an upright position.

Also needed is a rugged, simple, inexpensive, lightweight exoskeletal appliance that functions primarily with resilient components for energy storage and retrieval, yet still permits relatively un-constrained ambulation.

SUMMARY OF THE INVENTION

An illustrative embodiment of this invention comprises:

Exoskeletal struts, each on the left and right, strapped alongside the calves, thighs and upper body;

Pivoting, preferably adjustably limited, hinges, linking the exoskeletal struts at the ankle, knee and hip-joints;

Linear bearings pivoting co-axially at the hip-joints, provide travel for horizontal caliper pistons which are rigidly attached to transverse load/torque arm;

Caliper links pivotably link upper body and thigh struts respectively, to a load/torque arm and an associated differential cross-strut; and A mounting plate for a payload (such as an equipoising arm plus associated camera or tool assembly) is rigidly attached to the torque/load arm, which is rigidly connected to pistons. The attached equipoising arm may comprise one or more equipoising links. The arm may articulate at one or more points, including at the mounting location. "Equipoising" means counterbalancing, and does not necessarily indicate that the arm is iso-elastic or counters forces evenly throughout the arm's excursion. Iso-elastic arms though can be used with the invention.

An illustrative embodiment of the invention provides that the approximate angular attitude of the caliper pistons is divided between the momentary angles of upper body and thigh struts, during upright operation, as well as squatting or bending over.

Differential thigh excursions, such as excursions of strut from the vertical caused, by ambulation, are accommodated by the caliper thigh links interaction with the cross-strut. The differential thigh excursions cause the caliper thigh links to cause the cross-strut to pivot about the transverse torque/load arm, thereby dividing and equalizing the angular excursions of the thigh struts. Thus, normal walking motions are not significantly restricted.

The caliper action of the pistons with respect to the momentary angles of chest and thigh struts functions to keep the mounting plate nominally vertical, and thus likewise preserve the approximate verticality of the hinge pins of any attached articulated load-bearing arm-type structure—without any distinct upper-body torque loading on the operator that would be caused by the mounting plate departing significantly from vertical.

In an illustrative embodiment of the invention, a pulley assembly at ankle, knee and hip joint locations permit interconnection of resilient assemblies (resilient components and connecting cables) which are preferably arranged to be nearly slack when the operator is standing 'upright' and tensioned only when the operator is bending or squatting. The resilient assemblies run alongside chest, thigh and calf struts and around the ankle, knee and hip pulleys to terminate at attachments at either end of the torque/load arm. These resilient assemblies function to draw in the caliper pistons and the rigidly attached torque/load arm to resist bending/squatting motions and bias thigh and chest struts to a straightened upright standing position.

Possible benefits of the illustrative embodiment of the invention in use are as follows:

Torque on the operator, particularly on the upper body from a payload, for example, an equipoising (counter balancing) arm (or any forward cantilevered load) is reduced or eliminated compared to may conventional systems. Generally, the payload torque can be resisted by leaning slightly back from plumb. Muscular effort is reduced or minimized because the torque load is manifest at substantially right angles to the caliper pistons and does not contribute a force vector that would tend to collapse or expand the caliper and influence the momentary angle of the linked upper body, thighs, calves, etc.

Payload weight is transmitted serially along the exoskeletal struts and is directed to the ground, instead of being carried entirely or primarily by an operator's back, legs, ankles or feet.

The strain of squatting or bending over is resisted serially and cumulatively by the stretched resilient component acting to draw in the caliper pistons and straighten up the chest, thigh and calf struts.

Preferably, there is little or no interference with normal ambulation. Walking thigh excursions are alternately and substantially "equalized" by the differential cross-strut, instead of being additively transmitted to the caliper mechanism and displace the pistons from their preferably level attitude.

In an exemplary embodiment of the invention, the default, spring-loaded position of the exoskeleton is 'standing erect' so it can be easily 'put on' by leaning it against a wall and stepping into the 'shoe plates' from behind. The calf, thigh and chest straps can then be attached and an equipoising arm, for example, can then be mounted.

An illustrative embodiment of the novel load and torque bearing caliper exoskeleton of the invention has some or all of the following features: simple, rugged, lightweight, self-contained and inexpensive compared to actuated, servo-controlled exoskeletons, and requires no on-board or external power source.

The caliper exoskeleton invention can be used with 'person-carried' versions of tool-supporting arms such as equipoising or counterbalancing arms manufactured by Equipois Inc. or camera stabilizers such as Steadicam® manufactured by The Tiffen Company, LLC.

BRIEF DESCRIPTION OF THE DRAWINGS

FIG. 2b is a front elevation of the exoskeleton assembly of FIG. 2a shown with reference to a human figure, and depicting an illustrative payload-attachment location an exoskeleton assembly without the payload.

DETAILED DESCRIPTION OF THE INVENTION

Figure 1:
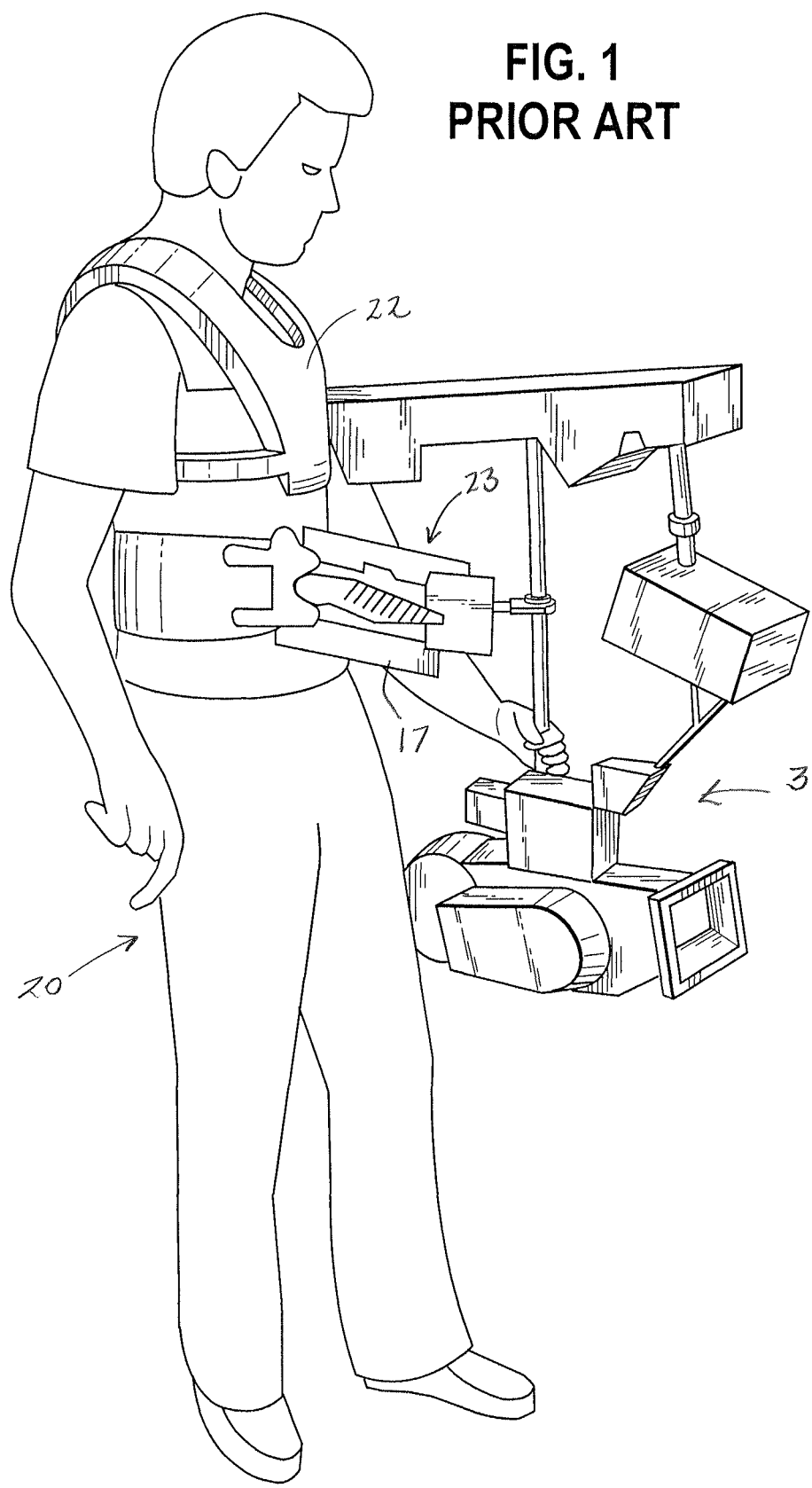
FIG. 1 shows an operator employing a prior-art 'vest' to mount an articulated support arm and associated payload.

FIG. 1 shows operator 20 employing a prior-art 'vest' 22 to mount an articulated support arm 17 and associated payload 3 (the combination as shown being marketed as the Steadicam® camera stabilizer, sold by The Tiffen Company, LLC). Vest 22 is tightly strapped to the upper body and the proximate end of arm 17 is adjustably attached to payload mounting structure 23 so that several arm hinge pins (not specified in the drawing) remain substantially vertical when the operator is standing upright. Because the torque load of the camera payload acts primarily on the upper body, it must be continuously resisted by the musculature surrounding the back vertebra—particularly the pair of erector spinae muscles that flank the spine. Certain maneuvers require the payload to be pushed as far as two feet or more further away from the operator's body than shown, which greatly increase the torque load. The weight load is of course also borne by the operator's torso, legs and feet, and cumulatively adds to fatigue. Bending and squatting maneuvers (to respectively clear low doorways or lower the minimum lens height) are only reluctantly attempted because once the hinge pins are no longer vertical, the arm and payload fall forward away from the operator with increasing force and must be additionally resisted with the operator's arms and back muscles.

Figure 2A:
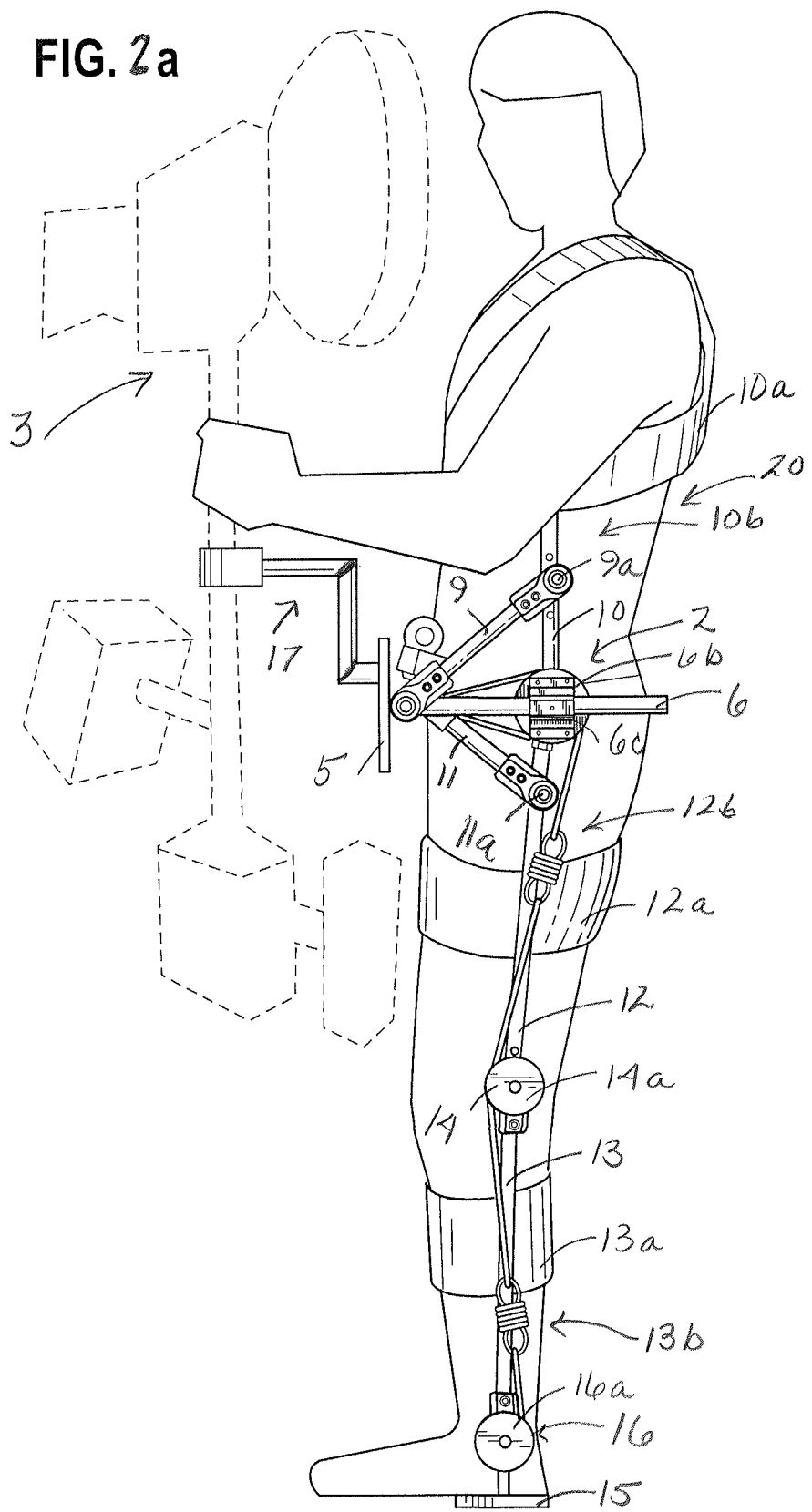
FIG. 2a is a side elevation of an exoskeleton assembly shown attached to a human figure and payload according to an illustrative embodiment of the invention.

FIG. 2a is a side elevation of an illustrative embodiment of an exoskeleton assembly 1 shown attached to a reference human FIG. 20 and to payload 3 by means of articulating support arm 17 attached to mounting plate 5. For simplicity the term "mounting plate" or "mounting component" will be used for any mounting device for attachment of a payload to the exoskeleton structure. The specific configuration of the mounting plate will depend at least in part on the type of payload to be attached. Other examples of mounting components include receptacles and pin combinations. The position of the mounting plate will de described at times as vertical, but it should be understood that the plate could also be horizontal or angled. In particular embodiments of the invention, the mounting component will substantially maintain its optimal relative position to the vertical even when a user is in a non-erect position such as squatting or sitting.

(Note that bilateral right side counterparts can exist for all the following left-side components but are not specifically here described). Foot plate 15 and calf, thigh and chest struts 13, 12, 10 correspond to the position of the operator's foot, calf, thigh and chest to which they are respectively attached by foot plate 15, and calf, thigh and chest straps 13a, 12a, 10a and pivotally interconnected, for example by ankle, knee and hip swivel joints 16, 14, 6b, which may be adjustably limited.

Joint articulation limits can be set by adjustable stops (not shown) of conventional design so that, for example, knee excursions can be mechanically limited to prevent the associated human knee joint from being biased rearward of its normal straightened position. Likewise, hip joint stops can prevent the thighs from being forced to the rear of their normal upright articulation. Various stops can be used. For example, by limiting the travel of piston 6 through left caliper linear bearing 6a by including a protrusion on the piston, such as a bolt, thigh strut 12 and chest strut 10 would be prevented from swinging back past vertical.

Caliper assembly 2 comprises chest and thigh links 9 and 11 and their swivel connections between chest and thigh struts, and load arm 4 (visible in FIG. 2b) which is rigidly associated with piston 6. The momentary posture of the operator produces a corresponding orientation of thigh and chest struts 12, 10, thus driving piston 6 fore and aft within linear bearing 6a. Mounting plate 5 is rigidly associated with load arm 4 and remains substantially vertical as long as piston 6 remains substantially horizontal, provided these components are set up in this relative configuration. More broadly, mounting plate 5 remains substantially in the same relative angular position to piston 6. Specific functioning of caliper assembly 2 and its remaining components will be detailed below.

FIG. 2b is a front elevation of an exemplary embodiment of exoskeletal assembly 1 shown with reference to human FIG. 20 and illustrating the relationship of the bilateral chest, thigh, calf and foot components to analogous human body parts. Chest, thigh and calf struts 10, 12, 13 correspond to and preferably closely parallel human chest, thighs, calves and feet, and are interconnected by swiveling hip, knee and ankle joints 6b, 7b (visible in FIG. 4), 14 and 16, that may be adjustable and limited in rotation. Limitation and adjustment degrees can be selectable. Left and right caliper assemblies 2 and 2a flank a payload-attachment component location shown in FIG. 2b as mounting plate 5 and rigidly associated with torque/load arm 4.

Figure 3:
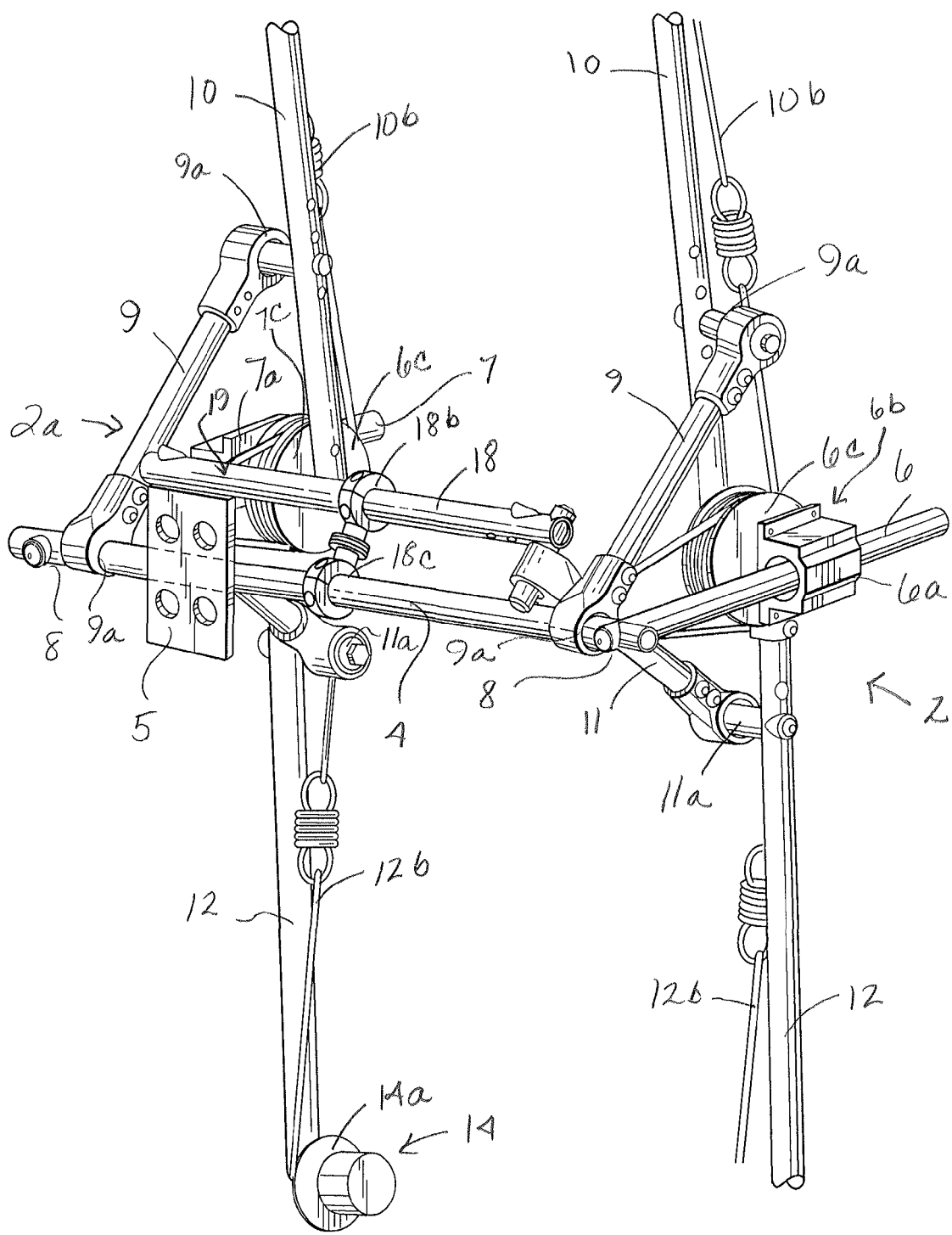
FIG. 3 is a quarter-view illustrating bi-lateral components of a portion of a caliper-exoskeleton according to an illustrative embodiment of the invention.
Figure 4:
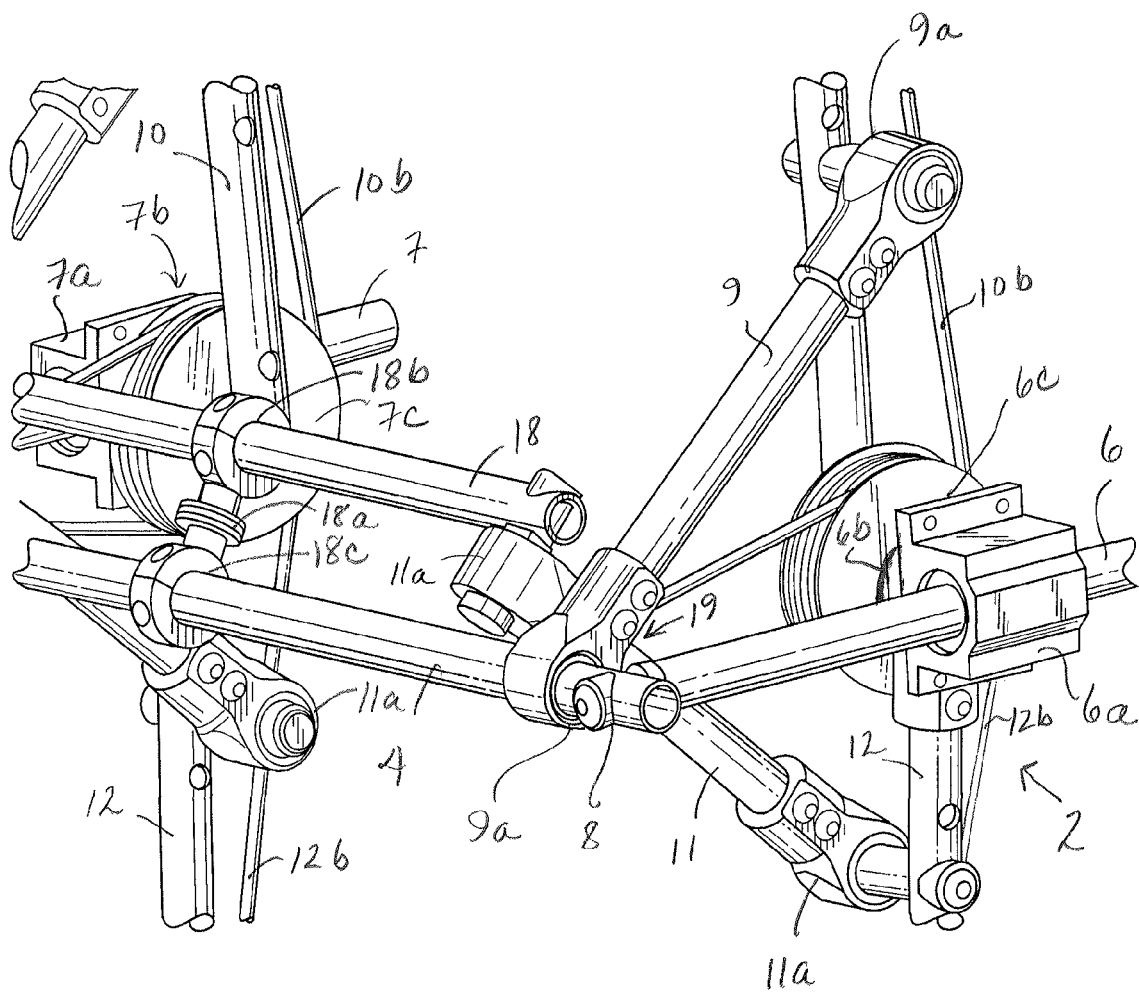
FIG. 4 is an enlarged view of components of FIG. 3.

FIG. 3 is a perspective quarter-view showing the bi-lateral components of an illustrative embodiment of a portion of exoskeletal assembly 1 and depicting left and right caliper assemblies 2 and 2a. FIG. 4 is a close-up view of a portion of FIG. 3. Chest struts 10 connect to thigh struts 12 by a multi-axis 'hip joint' swivel 6b, which in this illustrative embodiment is adjustably limited and arranged to permit the limited thigh rotations associated with walking, changing direction, squatting, and other activities.

Bilateral caliper assemblies 2 and 2a include linear bearings 6a, 7a that swivel about mounting axles around which chest struts 10 and thigh struts 12 also swivel.

which guide the fore/aft travel of caliper pistons 6, 7. Pistons 6, 7 are rigidly connected to the left and right extremities of transverse torque/load arm 4. Caliper chest links 9 and end-swivels 9a connect chest struts 10 to torque/load arm 4 as seen for example in FIG. 3. Caliper thigh links 11 can be configured to have limited motion, and preferably the degree of limitation can be selectable. End swivels on the end of each caliper link can swivel as required in two axes (so as not to bind) during thigh excursions. End swivels 11a connect thigh struts 12 to differential cross-strut 18. Clamp 18b and intervening one-axis swivel 18a and clamp 18c rigidly connect, for example in two of three substantially mutually perpendicularly axes, differential cross-strut 18 to the torque/load arm 4, preferably at torque/load arm 4 center.

Caliper assemblies 2, 2a thus provide that the momentary forward elevations of the left and right thigh struts 12 (such as during walking) are divided by differential cross-strut 18 to yield the net elevation of its central clamp 18b, and thus, by means of swivel 18a and clamp 18c, produce the resultant elevation of transverse load/torque arm 4 and the connected forward ends of pistons 6, 7.

The left and right caliper assemblies 2, 2a therefore divide the angle between the nominally parallel chest struts 10 and the variously non-parallel (during walking) thigh struts 12 and yield the net angle—nominally horizontal even when squatting or ambulating—of the left and right caliper pistons 6, 7, and likewise, by means of the rigidly connected torque/load arm 4, the nominally vertical attitude of payload mounting plate 5.

The illustrative embodiment includes resilient assemblies 10b and 12b, which consist of resilient components such as springs or bungee cords (indicated diagrammatically) in series with connecting cables running respectively under and over independent pulley pairs co-axially associated with linear bearings 6a, 7a to terminate at attachments 19, 19a on torque/load arm 4. (The function of these resilient assemblies will be further detailed in FIGS. 5-7.)

FIG. 4 is a close-up view that includes left caliper assembly 2 components and details the coaxial arrangement of caliper hip joint swivels 6b, pulley pair 6c and linear bearing 6a. Rigid right-angle connector 8 attaches piston 6 to transverse torque/load arm 4. Note that hip joint 6b may optionally include a second swivel axis (not shown) co-axial with thigh strut 12 to permit selectively limited thigh rotation during walking, squatting, etc.

The single axis of upper caliper thigh link swivel 11a is preferably substantially parallel to caliper chest link 9, and the single axis of lower caliper thigh-link swivel 11a is substantially parallel to torque/load arm 4 in order to determine, in combination, the piston travel for various torso bending angles and functions of differential cross-strut 18, which divides the thigh angle excursions due to ambulation.

Figure 5:
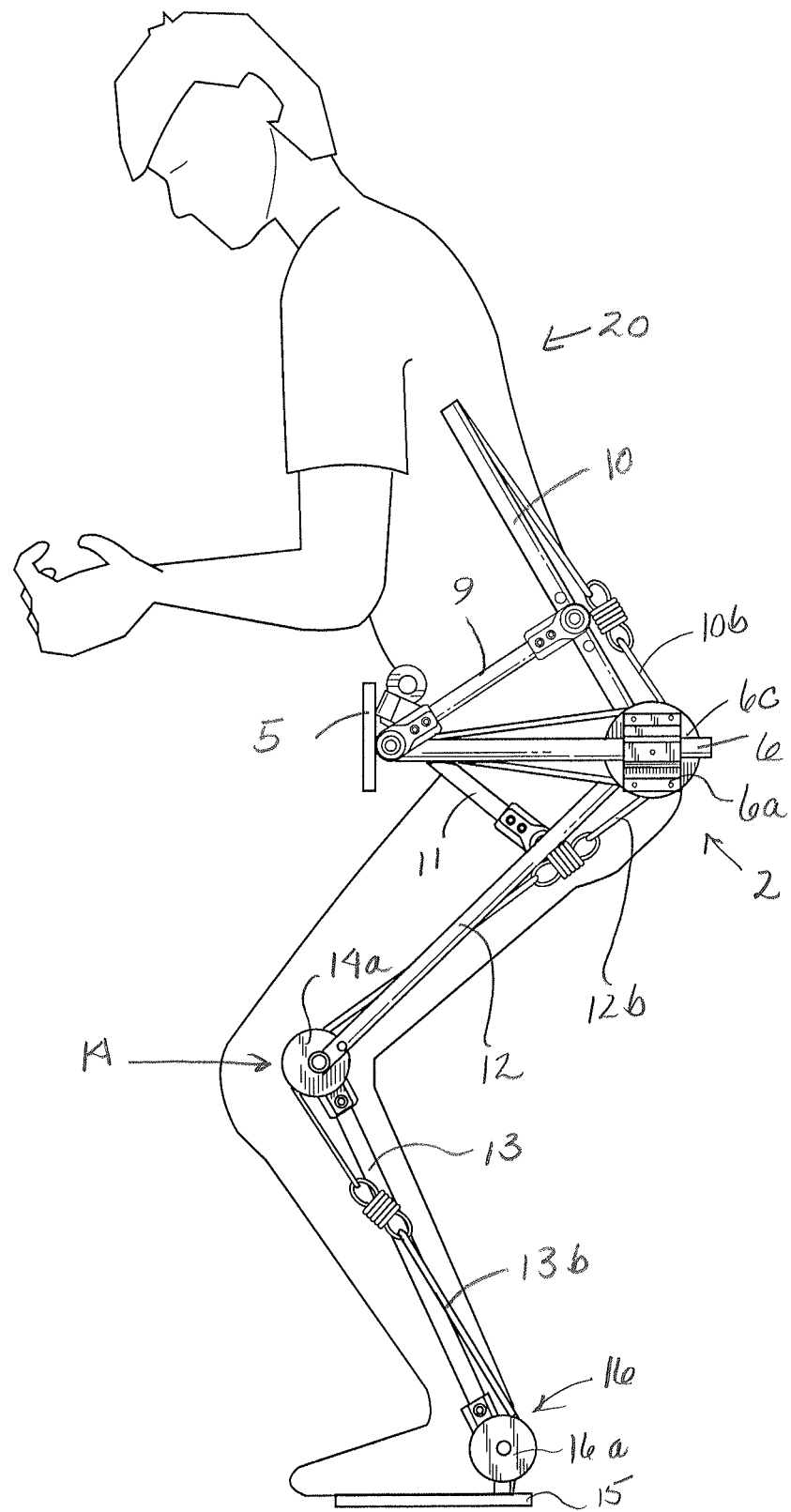
FIG. 5 is a side view of an exoskeleton assembly articulated into a squatting position and superimposed on a squatting human wearer according to an illustrative embodiment of the invention.

FIG. 5 is a side view of exoskeletal assembly 1 articulated into a squatting position and superimposed on similarly contorted human FIG. 20. Struts 10, 12 are bent substantially symmetrically forward into an acute angle from the vertical. Links 9 and 11 operate to drive piston 6 forward but substantially maintain its level attitude so that payload mounting plate 5 remains substantially vertical (which reduces or eliminates the possibility of any attached articulated arm plus payload lurching away from an operator—as has been the case with prior art vests.)

Ankle and knee pulleys 14a, 16a lead interconnected foot, calf and thigh resilient assembly 12b cable over caliper hip joint pulley 6a to termination 19 at torque/load arm 4 (shown in FIG. 4). Chest resilient assembly 10b cable also runs over the remaining paired caliper hip joint pulley 6a to termination 19 and the combined parallel resilient force additively draws the forward end of pistons 6, 7 (visible in FIG. 4) rearward to impel the torso back to a substantially erect standing position via caliper links 9, 11. The resulting force acts to counter the forces produced by a payload mass on the squatting torso of the operator.

Figure 6A:
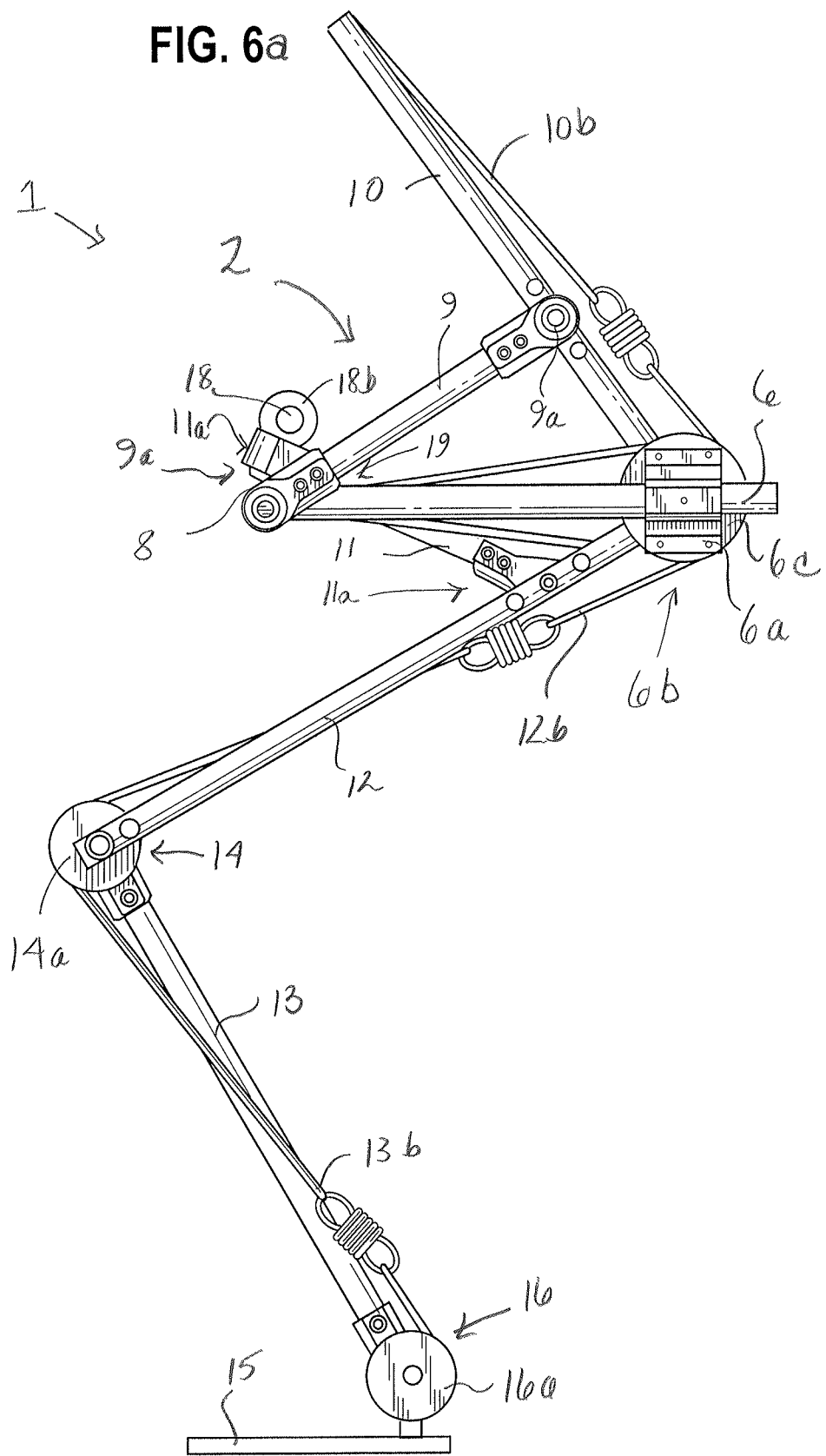
FIG. 6a is a side elevation of a caliper exoskeleton articulated into a squatting position, illustrating the function of the caliper mechanism according to an illustrative embodiment of the invention.

FIG. 6a is a side elevation of caliper exoskeleton assembly 1 according to an illustrative embodiment of the invention. FIG. 6a shows assembly 1 exoskeleton articulated into a squatting position, illustrating diagrammatically the function of left caliper assembly 2 in concert with resilient assemblies 10b, 12b, 13b (which each consist of resilient components in series with connecting cables) adapted to run over the various intervening pulley sets 16a, 14a, 6c. It can be seen that the resilient force—nominally slack when the torso (and associated exoskeletal assembly 1) is standing substantially upright—increasingly counters the strain of squatting down or bending over by drawing piston 6 rearward and urging chest, thigh and calf struts 10, 12, 13 to resume an upright, more columnar, and typically less stressful stance.

Also, note that in a squatting position, the attitude of a payload mounting plate 5 (such as shown in FIG. 3) would remain substantially vertically with respect to piston 6 and would tend not, therefore, to bias an attached articulating arm to fall away violently from the operator.

Figure 6B:
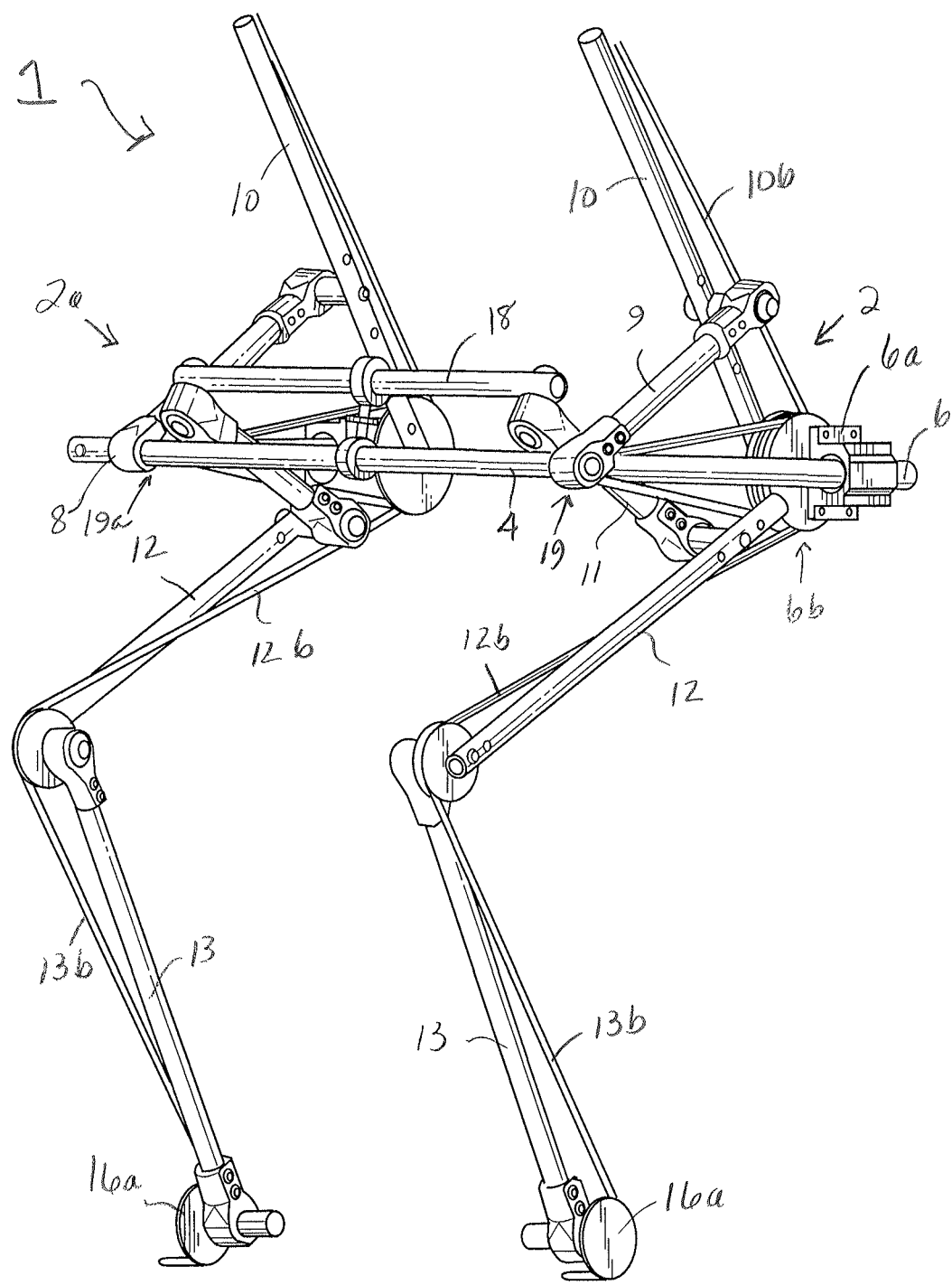
FIG. 6b is a quarter-side view of the exoskeleton assembly shown in FIG. 6a illustrating the load leveling function of the caliper mechanism in a squatting position according to an illustrative embodiment of the invention.

FIG. 6b is a perspective quarter-side view illustrating the load leveling function of caliper assemblies 2 and 2a while in a squatting position according to an illustrative embodiment of the invention. FIG. 6b also shows the dual effect of the bilateral resilient assemblies 10b, 12b, 13b to draw back torque/load arm 4 and attached pistons 6, 7 through linear bearings 6a and 7a (not visible) and re-erect struts 10, 12, 13 with little or no alteration of the axial rotation of torque/load arm 4.

Figure 7:
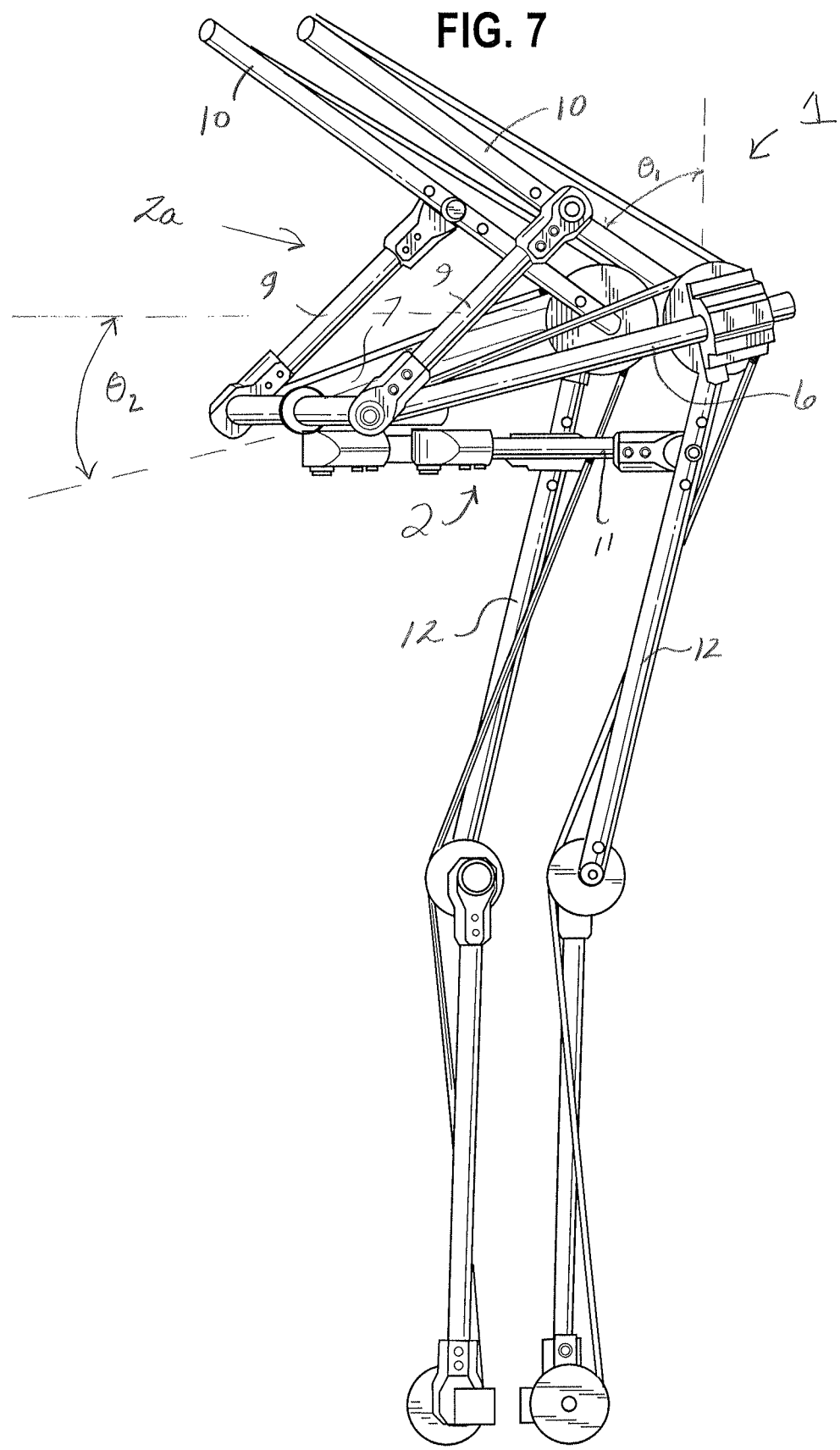
FIG. 7 is a quarter-view of an exoskeleton assembly showing the dividing function of the caliper between the momentary angles of the thigh and chest struts as the 'upper body' bends forward according to an illustrative embodiment of the invention.

FIG. 7 is a partial perspective-view of exoskeletal assembly 1 according to an illustrative embodiment of the invention. The dividing function of caliper assemblies 2 and 2a with regard to the momentary angles of the chest and thigh struts 10, 12 as the 'upper body' bends forward will de described with respect to FIG. 7. Note that although chest strut 10 leans forward approximately 60 degrees ($\theta_1$) from vertical, pistons 6, 7 only lean forward approximately 30 degrees ($\theta_2$) from the horizontal, and thus reduce tilting of hinge pin angles on arm 17 (such as shown in FIG. 2a). For example, arm 17 may have vertical hinge pins that would remain closer to vertical than would be the case with common prior-art vests made to lean 60 degrees forward. Thus, impelling the torso to return to an erect or vertical position would require less energy to do so than with from a similarly bent over position when wearing the common prior art vest.

Figure 8A:
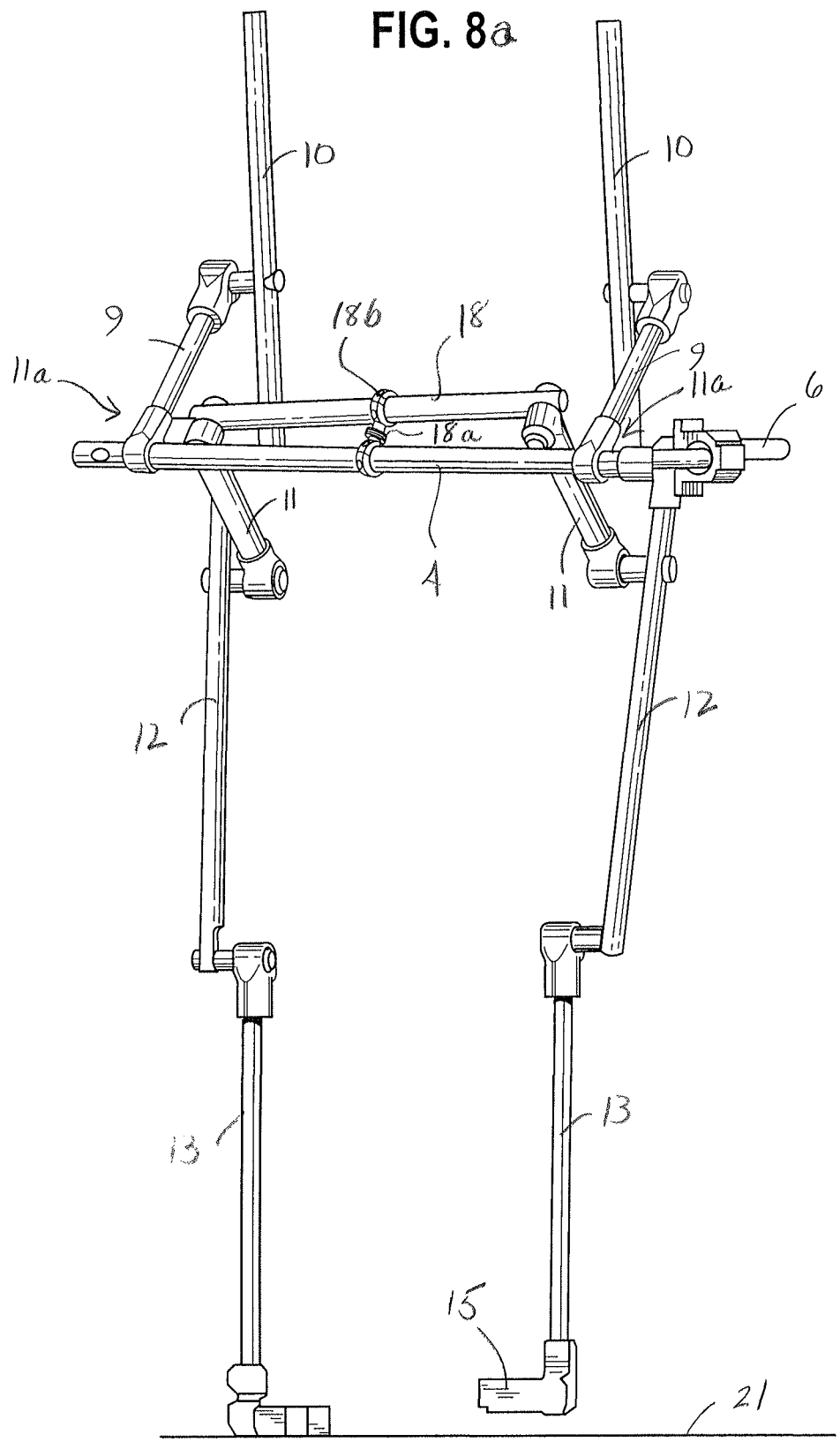
FIG. 8a depicts the angular effect on the differential strut during ambulation, and the divided, substantially equalized non-effect on the angle of the torque/load arm it supports according to an illustrative embodiment of the invention.

FIG. 8a is a perspective illustration of a portion of an exoskeleton assembly according to an illustrative embodiment of the invention. The angular effect on differential strut 18 during ambulation and the divided effect on the angle of torque/load arm 4 that differential strut 18 supports will be described pursuant to FIG. 8a. Differential strut 18 is shown at an angle to the horizontal during ambulation. As left footplate 15 is raised above ground level 21, left thigh strut 12 is articulated upward and right foot remains grounded; yet, due to the dividing function of differential strut 18, torque/load arm 4 is not impelled upward and remains substantially level.

Figure 8B:
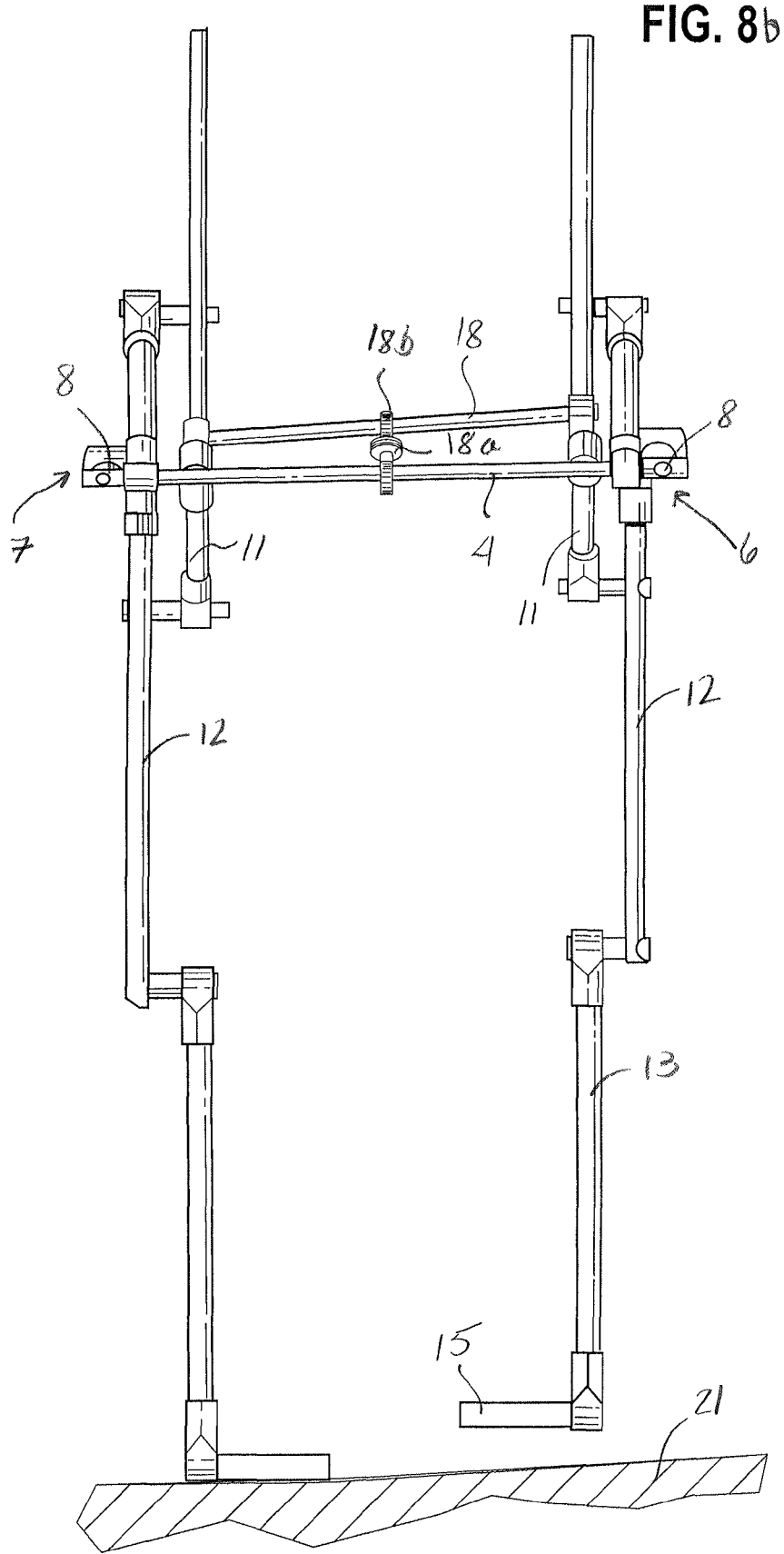
FIG. 8b is a front view of the assembly of FIG. 8a showing the off-level differential strut during ambulation (with the left foot-plate raised) and the torque/load arm remaining substantially level according to an illustrative embodiment of the invention.

FIG. 8b is a front elevation showing a different view of differential strut 18 according to the illustrative embodiment of FIG. 8a. FIG. 8b more clearly shows differential strut 18 at an angle to the horizontal during ambulation.

Figure 9:
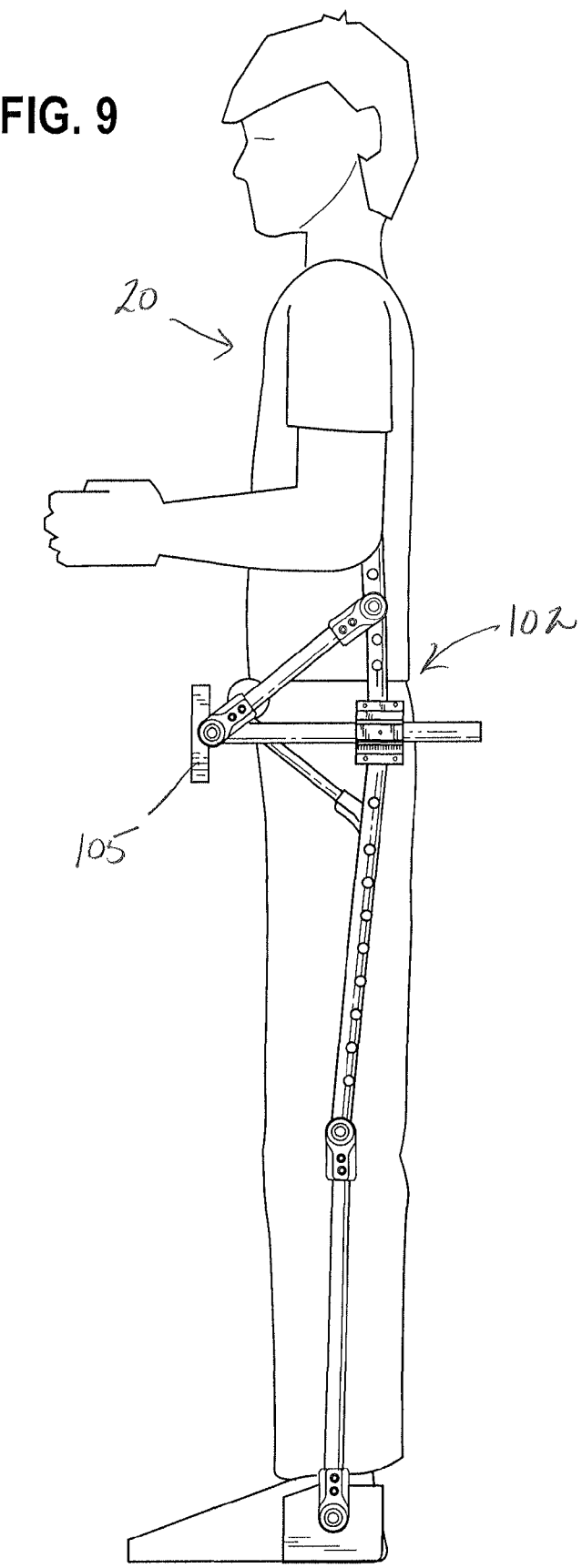
FIG. 9 is a side elevation illustrating an exoskeleton assembly without the resilient assemblies and associated pulleys according to an illustrative embodiment of the invention.

FIG. 9 is a side elevation of an exoskeleton assembly according to an illustrative embodiment of the invention. The embodiment shown includes components associated with FIGS. 3-8b except the resilient assemblies and associated components such as the pulleys. In this configuration caliper assembly 102 would still maintain the essential relative verticality of payload mounting plate 105, even during ambulation or throughout a symmetrical squatting maneuver; however it would not supply resilient biasing to assist the human operator in returning to an erect standing position.

Various embodiments of the invention have been described, each having a different combination of elements. The invention is not limited to the specific embodiments disclosed, and may include different combinations of the elements disclosed or omission of some elements and the equivalents of such structures.

While the invention has been described by illustrative embodiments, additional advantages and modifications will occur to those skilled in the art. Therefore, the invention in its broader aspects is not limited to specific details shown and described herein. Modifications may be made without departing from the spirit and scope of the invention. Accordingly, it is intended that the invention not be limited to the specific illustrative embodiments, but be interpreted within the full spirit and scope of the appended claims and their equivalents.

The invention claimed is:

1. An exoskeleton assembly comprising:
an upper body support assembly;
a lower body support assembly pivotally connected to the upper body support assembly;
a caliper assembly connected to the lower body support assembly and connected to the upper body support assembly;
wherein the caliper assembly comprises:
a torque/load arm having a left side and a right side;
a differential strut having a left side and a right side, the differential strut attached to and spaced apart from the torque/load arm;
a left caliper upper body link pivotally attached to the left upper body support assembly and pivotally attached to the left side of the torque/load arm;
a right caliper upper body link pivotally attached to the right upper body support assembly and pivotally attached to the right side of the torque/load arm;
a left caliper lower body link pivotally attached to the left lower body support assembly and pivotally attached to the left side of the differential strut;
a right caliper lower body link pivotally attached to the right lower body support assembly and pivotally attached to the right side of the differential strut;
a left piston fixedly attached to the left side of the torque/load arm and slidably attached to the left upper body support assembly and the left lower body support assembly combination;
a right piston fixedly attached to the right side of the torque/load arm and slidably attached to the right upper body support assembly and the right lower body support assembly combination; and
a mounting component fixedly attached to the torque/load arm;
wherein differential thigh excursion angles are transmitted by the right caliper thigh link and the left caliper thigh link and thus divided by angular excursions of the differential cross-strut pivoting relative to the torque/load arm.

2. The exoskeleton assembly of claim 1:
wherein the lower body support assembly includes:
a left thigh strut having a lower end and an upper end;
a left calf strut having a lower end and an upper end;
the left thigh strut lower end pivotally attached to the left calf strut upper end;
the left calf lower end pivotally attached to a left footplate;
a right thigh strut having a lower end and an upper end;
a right calf strut having a lower end and an upper end;
the right thigh strut lower end pivotally attached to the right calf strut upper end;
the right calf lower end pivotally attached to a right footplate;
wherein the upper body support assembly includes:
a left chest strut having a lower end and an upper end;
the left thigh strut upper end pivotally connected to the left chest strut lower end;
a right chest strut having a lower end and an upper end; and
the right thigh strut upper end pivotally connected to the right chest strut lower end.

3. The exoskeleton assembly of claim 2 wherein:
the left caliper upper body link is a left chest link pivotally attached to the left chest strut;
the right caliper upper body link is a right chest link pivotally attached to the right chest strut;
the left caliper lower body link is a left thigh link pivotally attached to the left thigh strut;

the right caliper lower body link is a right thigh link pivotally attached to the right thigh strut;

the left piston is slidably attached to the left chest strut and the left thigh strut combination; and the right piston is slidably attached to the right chest strut and the right thigh strut combination.

4. An exoskeleton assembly of claim 1 further comprising an equipoising (weight countering) arm attached to the upper body support assembly.

5. The exoskeleton assembly of claim 4 wherein the equipoising arm comprises a plurality of hinged segments, at least one of which is equipoising.

6. The exoskeleton assembly of claim 1 comprising:

a right pulley system; and a left pulley system;

each pulley system having a pulley at each body support joint and a first resilient component disposed around the pulleys with a termination at the torque/load arm;

wherein the first resilient components and pulleys are arranged so that the resilient components are more taught when a wearer of the exoskeleton is in a non-upright position as compared to an upright position; and wherein the resilient components and pulleys are arranged to draw in the pistons and cause the torque/load arm to resist excursions of the wearer from an upright standing position.

7. An exoskeleton assembly comprising:

a left thigh strut having a lower end and an upper end;

a right thigh strut having a lower end and an upper end;

a left chest strut having a lower end and an upper end;

a right chest strut having a lower end and an upper end;

a left calf strut having a lower end and an upper end;

a right calf strut having a lower end and an upper end;

the left thigh strut lower end pivotally attached to the left calf strut upper end;

the right thigh strut lower end pivotally attached to the right calf strut upper end;

the left thigh strut upper end pivotally connected to the left chest strut lower end;

the right thigh strut upper end pivotally connected to the right chest strut lower end;

the left calf lower end pivotally attached to a left footplate;

the right calf lower end pivotally attached to a right footplate;

a caliper assembly having a right side and a left side, the caliper assembly right side attached to the right chest strut lower end and further attached to the right thing strut upper end;

the caliper assembly left side attached to the left chest strut lower end and further attached to the left thing strut upper end the caliper assembly having:

a torque/load arm having a left side and a right side;

a differential strut having a left side and a right side, the differential strut attached to and spaced apart from the torque/load arm;

a left caliper chest link pivotally attached to the left chest strut and pivotally attached to the left side of the torque/load arm;

a right caliper chest link pivotally attached to the right chest strut and pivotally attached to the right side of the torque/load arm;

a left caliper thigh link pivotally attached to the left thigh strut and pivotally attached to the left side of the differential strut;

a right caliper thigh link pivotally attached to the right thigh strut and pivotally attached to the right side of the differential strut;

a left piston fixedly attached to the left side of the torque/load arm and slidably attached to the top end of the left thigh strut and bottom end of the left chest strut;

a right piston fixedly attached to the right side of the torque/load arm and slidably attached to the top end of the right thigh strut and bottom end of the right chest strut; and a mounting component fixedly attached to the torque/load arm;

wherein differential thigh excursion angles are transmitted by the right caliper thigh link and the left caliper thigh link and thus divided by angular excursions of the differential cross-strut pivoting relative to the torque/load arm.

8. The exoskeleton assembly of claim 1 wherein the mounting component is substantially vertical when the pistons are substantially horizontal.

* * * * *